United States Patent [19]

Yamawaki et al.

[11] 4,432,871
[45] Feb. 21, 1984

[54] IMMUNE ADSORBENT, ADSORBING DEVICE AND BLOOD PURIFYING APPARATUS

[75] Inventors: Maokuni Yamawaki; Shozo Suzuki; Tadaaki Furuta, all of Fuji, Japan

[73] Assignee: Asahi Kasei Kogyo Kabushiki Kaisha, Osaka, Japan

[21] Appl. No.: 339,368

[22] Filed: Jan. 15, 1982

[30] Foreign Application Priority Data

Jan. 22, 1981 [JP] Japan ............................. 56-7152
Jul. 21, 1981 [JP] Japan ........................... 56-112919

[51] Int. Cl.³ ........................................... B01J 20/22
[52] U.S. Cl. ............................. 210/195.1; 210/195.2; 210/266; 210/927; 502/401
[58] Field of Search ................. 210/645–647, 210/679, 690–692, 782, 787, 805, 806, 194, 195.1, 195.2, 196, 197, 259, 266, 295, 321.1, 321.3, 502, 512.1, 927; 252/426

[56] References Cited

U.S. PATENT DOCUMENTS 3,442,819  5/1969  Herbert ............................. 210/679
4,261,828  4/1981  Brunner et al. ..................... 210/927

*Primary Examiner*—Ivars C. Cintins
*Attorney, Agent, or Firm*—Sprung, Horn, Kramer & Woods

[57] ABSTRACT

An adsorbing material for an autoantibody and/or immune complexes is provided. The adsorbing material has an insoluble carrier and an organic low-molecular-weight compound containing a hydrophobic compound, which is fixed to the insoluble carrier. The adsorbing material may be used in an adsorbing device, which has a vessel having fluid inlet and outlet openings with the adsorbing material being contained in the vessel. The adsorbing device may be used in a blood purifying apparatus for absorbing and removing an autoantibody and/or immune complexes from blood plasma, which apparatus has (a) a plasma separating device and (b) a blood-plasma mixing device, which are disposed in series in a blood circulation passage, and (c) a plasma purifying device comprising the adsorbing device disposed in a plasma recycle passage connected to the blood circulation passage to introduce plasma, separated in the plasma separating device, into the mixing device.

16 Claims, 5 Drawing Figures

IMMUNE ADSORBENT, ADSORBING DEVICE AND BLOOD PURIFYING APPARATUS

BACKGROUND OF THE INVENTION

1. Field of the Invention

This invention relates to an immune adsorbent for specifically adsorbing and removing an autoantibody and/or immune complexes considered to have a close relation to various diseases due to immune reactions in the living body, an adsorbing device utilizing this immune adsorbent and a blood purifying apparatus comprising this adsorbing device.

2. Description of the Prior Art

As is well known, it has been considered that an autoantibody and/or immune complexes appearing in blood has a close relation causing or advancing of cancer, immune proliferative syndrome, autoimmune diseases (such as rheumatoid arthritis and systemic lupus erythematodes), and immume reactions (such as an allergic reaction or rejection at a transplantation of an internal organ).

Accordingly, it has been expected that specific adsorption and removal of an autoantibody and/or immune complexes from body fluid components, such as blood and plasma serum would be effective for preventing the advance of the above diseases, for relieving them and for expediting the remedy of these diseases.

As the immume adsorbent for attaining this object, there have been proposed an immune adsorbent comprising protein A fixed to an insoluble carrier, an acrylic acid ester type porous resin (for example, XAD-7 supplied by Rohm and Haas Co.) and a cation exchange member, such as carboxymethyl cellulose.

The immune adsorbent comprising protein A fixed to the insoluble carrier has a specific adsorbing capacity to an immuneglobulin and/or immune complexes, but, since protein A is a biologically active protein derived from yellow staphylococcus, this immune adsorbent is disadvantageous in that the starting material is difficult to obtain and the manufacturing cost is high. Furthermore, since the activity is unstable, deactivation is readily caused by handling at the fixing step or during storage after the fixing step. Moreover, when this immune adsorbent is used in the state where it is kept in contact with the body fluid, there is a risk of trouble occurring through the elution of protein A. Still further, it is very difficult to sterilize this immune adsorbent while preventing deactivation.

The acrylic acid ester type porous resin and carboxymethyl cellulose are insufficient in adsorbing capacity and adsorption specificity. Moreover, since they even adsorb albumin from the body fluid, an abnormal change in the osmotic pressure is caused and they cannot be used safely as a curing means.

SUMMARY OF THE INVENTION

The present invention is to solve the foregoing problems involved in the conventional techniques. More specifically, it is a primary object of the present invention to provide an immune adsorbent which can adsorb effectively and specifically an autoantibody and/or immune complexes, can stably maintain the activity, has a high degree of safety, can be sterilized with ease and is suitable for purification or regeneration of body fluid. It is another object of the present invention to provide an adsorbing device and blood purifying apparatus utilizing this immune adsorbent.

Other objects and advantages of the present invention will be apparent from the following description.

In accordance with a fundamental aspect of the present invention, there is provided an adsorbing material for an autoantibody and/or immune complexes, which comprises (a) an insoluble carrier and (b) an organic low-molecular-weight compound containing a hydrophobic compound, which is fixed to the insoluble carrier.

In accordance with another aspect of the present invention, there is provided an adsorbing device for an autoantibody and/or immune complexes, which comprises a vessel having fluid inlet and outlet openings, with the above-mentioned adsorbing material being contained in said vessel.

In accordance with still another aspect of the present invention, there is provided a blood purifying apparatus comprising the above-mentioned adsorbing device.

DESCRIPTION OF THE PREFERRED EMBODIMENTS

The substances to be adsorbed in the present invention are autoantibodies and immune complexes. More specifically, there can be mentioned autoantibodies, such as rheumtoid factors, anti-nuclear antibodies, anti-DNA antibodies, anti-lymphocyte antibodies, anti-erythrocyte antibodies, anti-thrombocyte antibodies, anti-acetylcholine receptor antibodies, serum demyelinating antibodies, anti-thyroglobulin antibodies, anti-microsome antibodies, and anti-colon antibodies, and immune complexes comprising an autoantibody and another substance, especially an antigen or an antigenic substance. These autoantibodies and immune complexes will be generally called "malignant substances" hereinafter. Autoantibodies and immune complexes having a close relation to the cause and advance of an autoimmune disease are especially preferred as substances to be adsorbed according to the present invention.

The hydrophobic compound used in the present invention is a compound having a solubility of not more than 100 millimoles, preferably not more than 30 millimoles, in one dl of a physiological saline solution at 25° C. In the case of a compound having a solubility in a physiological saline solution of more than 100 millimoles/dl, the hydrophilic property is increased too much and the affinity with immunoglobulin type compounds is low, with the result that the adsorbing capacity is drastically reduced.

Especially good results can be obtained when a hydrophobic compound, having at least one aromatic ring, is used as the hydrophobic compound. By the term "aromatic ring" is meant a ring having aromatic characteristics. For example, there are preferably used hydrophobic compounds having at least one aromatic ring selected from benzene type aromatic rings, such as benzene, naphthalene and phenanthrene rings; nitrogen-containing 6-membered rings, such as pyridine, quinoline, acridine, isoquinoline and phenanthridine rings; nitrogen-containing 5-membered rings, such as indole, carbazole, isoindole, indolizine, porphyrin and 2,3,2',3-pyrrolopyrrole rings; 6-membered rings having two or more nitrogen atoms, such as pyridazine, pyrimidine, sym-triazine, sym-tetrazine, quinazoline, 1,5-naphthyridine, pteridine and phenazine rings; 5-membered rings having two or more nitrogen atoms, such as pyrazole, iminazole, 1,2,4-triazole, 1,2,3-triazole, tetrazole, benzimidazole, imidazole and purine rings; oxygen-containing aromatic rings, such as norharman, perimidine, benzofuran, isobenzofuran and dibenzofuran rings; sulfur-containing aromatic rings, such as benzothiophene, thienothiophene and thiepine rings; oxygen-containing heterocyclic aromatic rings, such as oxazole, isooxazole, 1,2,5-oxadiazole and benzoxazole rings; sulfur-containing heterocyclic aromatic rings, such as thiazole, isothiazole, 1,3,4-thiadiazole and benzothiazole rings; and derivatives of the foregoing rings. Among these hydrophobic compounds, indole ring-containing hydrophobic compounds, such as tryptamine, provide especially good results. It is considered that this is due to the fact that, in effecting the bonding between a malignant substance and an indole ring-containing hydrophobic compound, the hydrophobic characteristic and molecular rigidity of said compound exert effective functions.

We made researches with a view to finding a hydrophobic compound which is capable of being put into practical use with high degree of safety and low expense, and we have found that hydrophobic amino acids and derivatives thereof adsorb and remove malignant substances highly specifically.

By the term "hydrophobic amino acid and derivative thereof" used herein are meant amino acids and derivatives thereof having a hydrophobic index, as defined by Tanford and Nozaki, J. Am. Chem. Soc., 184,4240 (1962) and J. Biol. Chem., 246,2211 (1971), of at least 1,500 cal/mol and a solubility in a physiological saline solution of lower than 100 millimoles/dl. For example, there can be mentioned lysine, valine, leucine, tyrosine, phenylalanine, isoleucine and tryptophane, and derivatives of these amino acids. Among these amino acids and derivatives, tryptophane and its derivatives give especially good results. These amino acids may be of the l- and d-configurations.

By the term "organic low-molecular-weight compound containing the hydrophobic compound" used in the present specification we mean (i) the hydrophobic compounds per se, (ii) derivatives of the hydrophobic compounds, or (iii) polymers of the hydrophobic compounds. The organic low-molecular-weight compounds should have a molecular weight of not higher than about 10,000, preferably not higher than about 1,000. Such compounds can be handled more easily at the step of fixing such compounds to an insoluble carrier and can be preserved more easily after the fixation than a natural polymer such as protein A (having a molecular weight of about 42,000). Furthermore, even if these compounds, having a molecular weight of not higher than about 10,000, are dissolved from the insoluble carrier, since the allergic property of these compounds to the living body is negligibly small, safety can be ensured, and the sterilizing operation can be accomplished very easily. The derivatives of the hydrophobic compounds can be obtained by chemical modification of the hydrophobic compounds. The term "chemical modification" means a reaction of the type wherein a compound capable of being bonded through a covalent bonding is introduced to the hydrophobic compound. For example, preferable derivatives of a hydrophobic amino acid can be obtained by chemically modifying, e.g., amidating or iminating the amino group and/or esterifying or amidating the carboxyl group of the hydrophobic amino acid. The polymer of a hydrophobic compound can be obtained by homopolymerization of the hydrophobic compound or copolymerization of the hydrophobic compound with other copolymerizable compounds. As the hydrophobic compound to be polymerized, there can be used a vinyl derivative of an indole ring-containing compound, such as tryptamine, and a hydrophobic amino acid, such as tryptophane.

As the insoluble carrier, there can be used either a hydrophilic carrier or a hydrophobic carrier according to the present invention. When a hydrophobic carrier is used, it sometimes happens that non-specific adsorption of albumin to the carrier takes place. Therefore, use of a hydrophilic carrier is preferred.

The form of the insoluble carrier is not particularly critical, and any of a number of known forms may be used. For example, there may be used particulate, fibrous, hollow fibrous and film forms. From the viewpoints of the amount of the hydrophobic compound retained and easiness in handling as the immune adsorbent, it is preferred that the insoluble carrier be of a particulate or fibrous form.

In the case of the particulate carrier, it is preferred that the average particle size is 25 to 2,500 $\mu$m, especially 150 to 2,500 $\mu$m. The average particle size is determined by classifying the sample in running water by using sieves specified by JIS Z-8801, calculating the mean value of the upper limit particle size and the lower limit particle size for each class and then determining the weight average value as the average particle size of the calculated mean values. The shape of the particles is not particularly critical, although the spherical shape is preferred. If the average particle size is larger than 2,500 $\mu$m, the quantity of the adsorbed malignant substance and the adsorption speed are reduced, and if the average particle size is smaller than 25 $\mu$m, activation of the coagulation system or the adhesion of blood cells is readily caused. As the particulate carrier, there can be used agarose, dextran, cellulose, polyacrylamide, glass, silica and active charcoal carriers. A hydrophilic carrier, having a gel structure, gives especially good results. Known carriers customarily used for fixation of enzymes or affinity chromatography can be used without any particular limitation.

As the particulate carrier, there may be used porous particles, especially porous polymers. The hydrophobic compound can be fixed to the surfaces of the porous polymer particles used in the present invention. There may be used polyamides, polyesters, polyurethanes, vinyl compound polymers and other known polymers that have a porous structure. Vinyl compound type porous polymer particles rendered hydrophilic by a hydrophilic monomer give especially good results.

As the carrier material, there is preferably used a hydroxyl group-containing copolymer, and especially good results can be obtained when a copolymer, comprising vinyl alcohol units as the main constituent, is used as the carrier. A carrier composed of a crosslinked copolymer, comprising vinyl alcohol units as the main constituent, has a low mutual action with solutes, such as proteins in plasma, because of its hydrophilic characteristic, and non-specific adsorption can be reduced to a minimum level. Furthermore, this carrier is excellent in that it does not react with the complement system or coagulation system in plasma. Moreover, this carrier is excellent in various physical properties. For example, since the carrier is excellent in heat resistance, sterilization is possible, and the carrier is excellent in physical and mechanical strengths, which are inherent characteristics of a synthetic polymer. Even when this carrier is used for a whole blood adsorbing member, the carrier exerts very excellent effects of controlling the formation of thrombus and reducing the non-specific adhesion of hematocyte components or the remainder of blood to a minimum level.

As the density of hydroxyl groups is increased in the crosslinked copolymer used in the present invention, the hydrophilic characteristic is increased, the mutual reaction with blood components can advantageously be reduced, and the active group density can be maintained at a high level when the copolymer is activated by an activating agent. However, since the crosslinking density (the content of the crosslinking agent) is reduced, the physical and mechanical strengths are degraded. It is, therefore, preferred that the hydroxyl group density be in the range of from 1.0 to 17 meq/g, especially 5 to 15 meq/g.

The hydroxyl group density can be determined by reacting the sample with acetic anhydride in pyridine as the solvent, measuring the amount of acetic anhydride consumed by the reaction with the hydroxyl group or measuring the weight change of the carrier and calculating the hydroxyl group density based on the measurement results. When 1 g of the dry carrier reacts with 1 millimole of acetic anhydride, the hydroxyl group density is 1 meq/g.

Crosslinked polymers, comprising vinyl alcohol units as the main constituent, can be synthesized by the polymerization of a hydroxyl group-containing monomer or the introduction of hydroxyl groups into a polymer by a chemical reaction. Both the processes may be adopted in combination. The radical polymerization process may be used for the polymerization. A crosslinking agent may be introduced by copolymerization at the polymerization step or by chemical reaction of a polymer (reaction between polymers or reaction of a polymer with a crosslinking agent). Both the processes may be adopted in combination.

For example, a crosslinked copolymer may be prepared by copolymerization of a vinyl monomer with a vinyl or acrylic crosslinking agent. As the vinyl monomer, there can be mentioned, for example, vinyl esters of carboxylic acids, such as vinyl acetate and vinyl propionate, and vinyl ethers, such as methyl vinyl ether and ethyl vinyl ether.

As the crosslinking agent, there can be mentioned, for example, allyl compounds, such as triallyl isocyanurate and triallyl cyanurate; diacrylates and dimethacrylates, such as ethylene glycol dimethacrylate and diethylene glycol dimethacrylate; polyvinyl ethers, such as butanediol divinyl ether, diethylene glycol divinyl ether and tetravinyl glyoxazale; polyallyl ethers, such as diallylidene pentaerythritol and tetraallyloxyethane; and glycidyl acrylates, such as glycidyl methacrylate. Other comonomers may be copolymerized.

As the vinyl copolymer, there is preferably used triallyl isocyanurate-crosslinked polyvinyl alcohol obtained by copolymerizing a vinyl ester of a carboxylic acid with a vinyl compound or allyl compound and hydrolyzing the obtained copolymer, because this copolymer gives a carrier excellent in strength and chemical stability.

In the case of a fibrous carrier, it is preferred that the fiber diameter be in the range of from 0.02 to 10 denier, especially 0.1 to 5 denier. When the fiber diameter is too large, the quantity of the adsorbed malignant compound and the adsorption speed are reduced. When the fiber diameter is too small, activation of the coagulation system, adhesion of hematocytes and clogging of the immune adsorbent are readily caused. For the fibrous carrier, there are ordinarily used regenerated cellulose fibers, nylon fibers, acrylic fibers, polyester fibers, polyvinyl alcohol fibers and other known fibers.

As the method for fixing the low-molecular-weight compound, containing the hydrophobic compound, to the surface of the insoluble carrier, there can be used any of a number of known methods, such as covalent bonding, ionic bonding, physical adsorption, embedding and precipitation-insolubilization on the polymer surface. From the viewpoint of preventing elution of the organic low-molecular-weight compound containing the hydrophobic compound, it is preferred that fixation and insolubilization be effected by covalent bonding. For this purpose, a known insoluble carrier-activating and bonding method, customarily used for the fixation of enzymes or for affinity chromatography, can be used in the present invention. If necessary, a molecule (spacer) having an optional length may be introduced between the insoluble carrier and the organic low-molecular-weight compound containing the hydrophobic compound. For example, there may be adopted a method in which the hydroxyl group of agarose is reacted and bonded with one isocyanate group of hexamethylene diisocyanate and the remaining isocyanate group is reacted and bonded with the amino, hydroxyl, sulfhydryl or carboxyl group of the organic low-molecular-weight compound containing the hydrophobic compound.

When the amount of the organic low-molecular-weight compound containing the hydrophobic compound, which is fixed to the carrier in the present invention, is in the range of from 0.1 to 50 mg, especially 1.0 to 30 mg, per m of the carrier, good results can be obtained.

The device for adsorbing malignant substances according to the present invention comprises a vessel having inlet and outlet openings and the above-mentioned adsorbing material being contained in said vessel.

Figure 1:
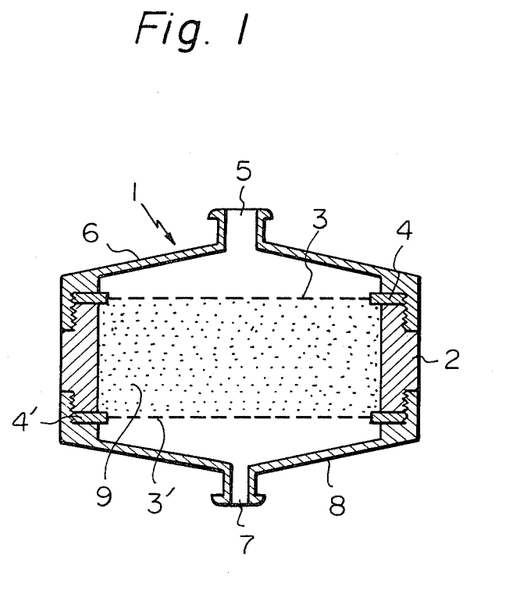
FIG. 1 is a sectional view illustrating one embodiment of the device for adsorbing malignant substances according to the present invention.

An embodiment of the adsorbing device 1 for adsorbing malignant substances according to the present invention is illustrated in FIG. 1. A cap 6 having a body fluid inlet 5 is screwed to one open end of a cylinder 2 through a packing 4 having a filter 3 spread on the inner side thereof and a cap 8 having a body fluid outlet 7 is screwed to the other open end of the cylinder 2 through a packing 4' having a filter 3' spread on the inner side thereof, and the immune adsorbent is filled and held between the filters 3 and 3' to form an immune adsorbent layer 9.

In the immune adsorbent layer 9, the immune adsorbent of the present invention alone may be contained, or, the layer 9 may be comprised of an adsorbent mixed with other adsorbents or the layer 9 may be comprised of a layer or layers of the immune adsorbent of the present invention superposed upon another adsorbent layer or layers. As such other adsorbents, there can be used other immune adsorbents for malignant substances (antigens), such as DNA and active charcoal having an adsorbing capacity in a broad range. In this case, the clinical effect attained can be expected to be in a broad range, because of the synergistic actions of the immune adsorbents. When the adsorbing device is used for ectosomatic circulation, it is preferred that the volume of the immune adsorbent layer 9 be about 50 to about 400 ml.

When the adsorbing device of the present invention is used for ectosomatic circulation, the following two methods are ordinarily adopted. According to one method, blood taken out from the interior of the living body is separated into the plasma component and the hematocyte component by a centrifugal separator or membrane type plasma separator; the plasma component is passed through the adsorbing device to be thereby purified; and the purified plasma component is combined with the hematocyte component and returned to the interior of the body. According to the other method, blood taken out from the interior of the living body is directly passed through the adsorbing device to be thereby purified.

When a particulate carrier, having an especially fine particle size, is contained in the adsorbing device or when a fibrous carrier is contained at a high density in the adsorbing device, so as to increase the surface of the insoluble carrier in the adsorbing device, the pressure loss is remarkably increased by the adhesion of hematocytes and other causes, and the circulation of blood becomes impossible within a very short time. Accordingly, in order to remove malignant substances at a high efficiency, it is preferred that plasma be purified in the adsorbing device. As such clinical blood purifying apparatuses, there can be used a blood purifying apparatus which comprises a blood introduction zone, a purified blood discharge zone, a blood circulation passage, including a plasma separating device and a blood-plasma mixing device, and a plasma recycle passage connected to said blood circulation passage to introduce plasma separated in the plasma separating device into said mixing device through a plasma purifying device, said circulation passage and recycle passage being disposed between said blood introduction zone and said purified blood discharge zone, wherein said plasma purifying device is the above-mentioned adsorbing device of the present invention. In this blood purifying apparatus, blood introduced from the blood introduction zone is separated into concentrated blood and plasma by the plasma separating device, malignant substances are separated from the separated plasma by the plasma purifying device, and the purified plasma is mixed with blood in the blood-plasma mixing device.

In this blood purifying apparatus, the blood introduction zone is a zone for introducing blood into the purifying apparatus by a blood collector, including a shunt and an injection needle, and an assembly of a conduit, a cock, and, if necessary, a pump; and the purified blood discharge zone is a zone for discharging blood, purified by the blood purifying apparatus, from the blood purifying apparatus by an assembly of a conduit, a cock, and, if necessary, a blood pressure control valve, a shunt and an instillator. The first characteristic feature of the blood purifying apparatus of the present invention is that the blood circulation passage, including as the main members the blood-plasma mixing device and the plasma separating device, is connected to the plasma recycle passage, including as the main member the plasma purifying device for purifying plasma separated by the plasma separating device by adsorbing and removing malignant substances. The respective devices, circulation passage and recycle passage are connected to one another, if necessary, through valves, pumps and filters, so that the blood and/or plasma is circulated and recycled.

The blood purifying apparatus according to the present invention will now be described in detail with reference to the accompanying drawings.

Figure 2:
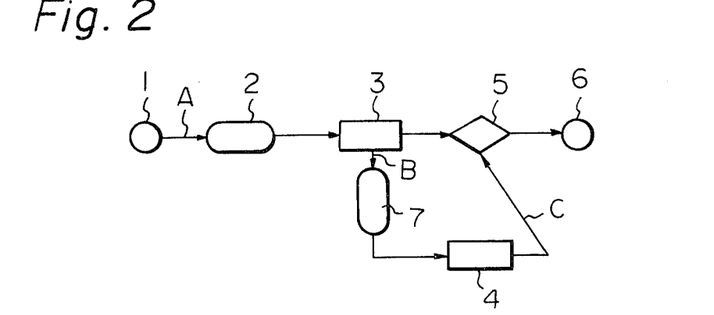
FIG. 2 is a diagram illustrating one basic embodiment of the blood purifying apparatus according to the present invention.

FIG. 2 is a diagram illustrating one embodiment of the basic structure of the blood purifying apparatus according to the present invention. The apparatus of the present invention will now be explained according to the flow of blood. Blood A is introduced from a blood inlet 1 of the blood introduction zone and transported to a plasma separating device 3 by using a pump 2, such as a roller pump, according to need. Plasma B, separated by the plasma separating device 3, is fed to a plasma purifying device 4 by using a pump 7, such as a roller pump, according to need, and malignant substances present in the plasma are removed in the plasma purifying device 4. Purified plasma C is supplied to a blood-plasma mixing device 5 where it is mixed with concentrated blood discharged from the plasma separating device 3, and the resulting purified blood is discharged from a blood discharge zone 6.

Figure 3:
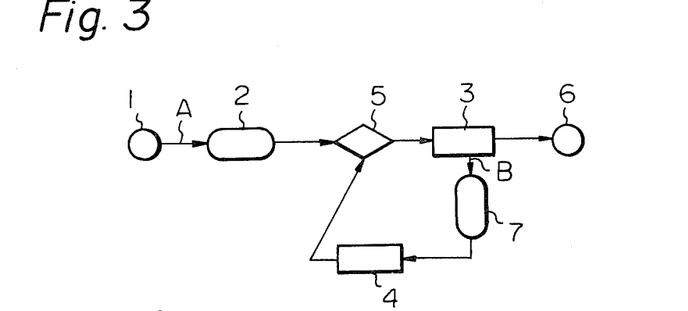
FIGS. 3 and 4 are diagrams illustrating other embodiments of the blood purifying apparatus according to the present invention.

FIG. 3 is a diagram illustrating another embodiment of the basic structure of the blood purifying apparatus of the present invention. This embodiment will now be described according to the flow of blood. Blood A is introduced from a blood inlet 1 of the blood introduction zone and transported to a blood-plasma mixing device 5 by using a pump 2, such as a roller pump, according to need. In the mixing device 5, blood is mixed with plasma B, and is then fed to a plasma separating device 3 and separated into plasma B and purified blood. The separated purified blood is discharged from a blood discharge zone 6, and the separated plasma is fed to a plasma purifying device 4 by using a pump 7, such as a roller pump, according to need. In the plasma purifying device 4, malignant substances present in the plasma are removed. Purified plasma is fed to the blood-plasma mixing device 5 and is mixed with blood A introduced from the blood inlet 1.

Of course, a blood purifying apparatus constructed by combining the basic structures shown in FIGS. 2 and 3 may be used in the present invention.

Figure 4:
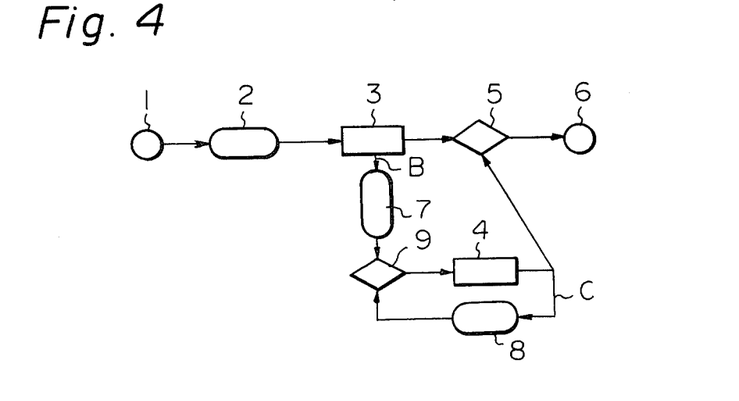

Furthermore, a circulation-recycle method shown in FIG. 4, in which a part of the plasma C, which has been subjected to the adsorption treatment, is fed to a plasma mixing device 9 where said part of plasma C is mixed with fresh plasma B, and malignant substances are then removed in the plasma purifying device 4, may also be used in the present invention.

As the plasma separating device used in the present invention, there can be mentioned a device including a porous filtering membrane and a centrifugal separation device.

Figure 5:
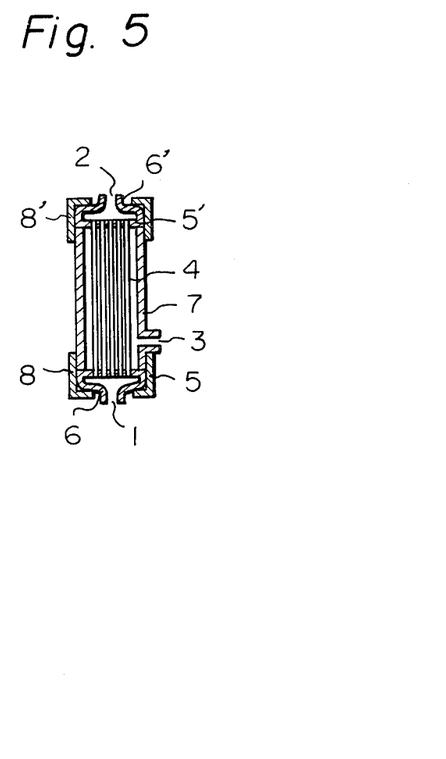
FIG. 5 is a sectional view illustrating one embodiment of the plasma separating device according to the present invention.

As the plasma separating device including a porous filtering membrane, there is preferably used a device having a structure shown in FIG. 5, in which the porous filtering device is arranged in parallel to a passage connecting an inlet and an outlet to each other. In order to perform filtration stably and at a high efficiency for a long time, it is preferred that the passage be made as narrow as possible. The shape of the porous filtering membrane is not particularly critical. For example, a planar membrane or a hollow fiber membrane may be used. It is preferred that a membrane molded in the form of a hollow fiber be used, so that the hollow portion acts as the flow passage.

FIG. 5 is a sectional view illustrating one embodiment of the plasma separating device used in the present invention. The device comprises a blood inlet 1, a blood outlet 2, a plasma outlet 3 and many hollow fibers 4 contained in the interior. Adhesive bonded and solidified portions 5 and 5' are formed on the terminal portions of the hollow fibers 4, and nozzles 6 and 6' connected to the blood inlet 1 and blood outlet 2, respectively, are clamped by caps 8 and 8', respectively, screwed to screw portions of a vessel proper 7. The space defined by the outer walls of the hollow fibers and the vessel proper 7 is a space in which separated plasma is temporarily stored. In this structure, blood is caused to flow in the hollow portions of the hollow fibers and plasma is transferred to the outside of the hollow fibers. A plasma separating device, having a structure in which blood is caused to flow outside the hollow fibers and plasma is caused to move in the hollow portions, may also be used in the present invention.

The plasma-separating porous membrane, used for the plasma separating device, is a membrane not allowing passage of the hematocyte components, but allowing substantial passage of the globulin compounds. It is preferred that a membrane, having fine through pores having an average pore size of 0.05 to 2.0 $\mu$m, especially 0.08 to 0.8 $\mu$m, which are distributed substantially uniformly on the surfaces of the membrane, be used and the water permeability of the membrane be at least 3 l/m² hr mmHg.

In order to stably obtain plasma without damaging hematocytes by using the plasma separating device, including the above-mentioned membrane, it is indispensable that the difference of the pressure between the blood inlet 1 and the plasma outlet 3 in the separating device shown in FIG. 5 should be controlled to 10 to 60 mmHg.

The material of the selective permeation membrane used in the present invention is not particularly critical. For example, there can be used polyethylene, polypropylene, polycarbonate, polyvinyl alcohol, polysulfone, cellulose acetate and polymethyl methacrylate.

As the plasma separating device utilizing centrifugal separation, there can be used any of a number or centrifugal separation devices, so far as blood is continuously introduced on one side and concentrated blood and plasma are independently discharged on the other side. A continuous centrifugal separator not provided with a sliding portion is especially preferably used.

The mixing device is used in the present invention for mixing purified plasma with concentrated blood, or blood from which plasma is to be newly separated, or for mixing purified plasma with plasma to be newly purified. It is preferred that mixing be completely accomplished by stirring or the like. However, the intended object can be attained sufficiently by a device for combining two fluid streams, for example, a Y-shaped connector.

In carrying out the present invention, in the passages shown in FIGS. 2 and 3, a buffer tank may be provided or another plasma separating or filtering device may also be provided to construct a multi-staged system.

Since the adsorption efficiency of the immune adsorbent of the present invention is very high, the particle size of the immune adsorbent can be increased or the packing density of the immune adsorbent can be reduced. Namely, a high blood or plasma permeation speed can be obtained irrespectively of the shape of the immune adsorbent layer. Accordingly, a large quantity of body fluid can be treated.

The body fluid is circulated in a continuous manner or discontinuously. An appropriate body fluid circulation method may be chosen and used according to clinical necessity or the equipment conditions.

As will be apparent from the foregoing description, the immune adsorbent, adsorbing device and blood purifying apparatus of the present invention are advantageous in that an autoantibody and/or immune complexes in the body fluid can be specifically and selectively adsorbed and removed at a high efficiency and in that the adsorbing device and blood purifying apparatus have a very compact structure and can be handled very easily with a high degree of safety. Moreover, they are advantageous in that the sterilization operation can be performed very easily and assuredly.

The present invention can be applied to the general method for purifying and regenerating body fluid, and is effectively utilized for safe and sure remedy of diseases concerning the immunoactivities of the living body, especially autoimmune diseases, such as rheumatoid arthritis and systemic lupus erythematodes.

The present invention will now be described in detail with reference to the following Examples that by no means limit the scope of the invention.

EXAMPLE 1

4-Aminodiphenylamine was bonded to CNBr-activated CH-sepharose 4B (supplied by Pharmacia Co., Sweden; average particle size=260 $\mu$m) according to customary procedures, and excessive active groups were blocked by ethanolamine. The retention quantity was determined by reacting and bonding the remaining primary amino groups of the hydrophobic compound with 4-phenylspiro[furan-2(3H)-1'-phthalan]-3,3'-dione ("Furlam ®" supplied by Roche Co.), conducting the measurement with fluorescent rays of 475 to 490 nm (exciting waves of 390 nm) and subtracting the physical adsorption quantity, obtained separately by using unactivated CH-sepharose 4B, from the measured quantity.

After blocking with ethanolamine, the adsorbing member was washed repeatedly with a 0.1 M acetic acid buffer solution having a pH value of 4 and a 0.1 M boric acid buffer solution having a pH value of 8.5, and the immune adsorbent was then washed with a physiological saline solution, hydro-extracted and used for the experiments.

In the adsorption experiment, plasma of a man suffering from rheumatoid arthritis was mixed with the adsorbing member at a volume ratio of 1:1 and the mixture was incubated at 37° C. for 3 hours.

The capacity of adsorbing and removing malignant substances of rhematoid arthritis, that is, rheumatoid factor (autoantibody) and immune complexes were determined as follows. The rheumatoid factor concentration was measured by the latex fixation test and the passive sensitized hematocyte agglutination test. According to the latex fixation test, the phenomenon, in which fixation of latex particles is caused when polystyrene latex particles on which human $\gamma$-globulin has been adsorbed is reacted with plasma of a patient containing the rheumatoid factor, is utilized for detection. More specifically, dilutions of plasma differing in concentration are prepared, and the rheumatoid factor concentration is evaluated, based on the plasma dilution ratio at which the fixation of latex particles is not caused. In the case of plasma containing the rheumatoid factor at a high concentration, the dilution ratio at which the fixation is negative is increased, but in the case of plasma containing the rheumatoid factor at a low concentration, the dilution ratio at which the fixation is negative is lowered.

According to the passive sensitized hematocyte agglutination test, sheep erythrocytes on which rabbit γ-globulin has been adsorbed are used, and other procedures are the same as those adopted in the latex fixation test. It is considered that the rheumatoid factor specificity is higher in the passive sensitized hematocyte agglutination test than in the latex fixation test.

A series of dilutions was prepared by using a glycine-containing saline buffer solution, and the dilution ratio at which the rheumatoid factor became negative was determined. The latex fixation test was carried out by using a kit supplied by Nippon Toketsu Kanso Kenkyusho. Similarly, the passive sensitized hematocyte test was carried out by using a kit (RAHA test kit) supplied by Fuji Zoki Seiyaku K. K.

The immune complex body concentration was measured according to the complement hemolysis method using polyethtylene glycol. According to this method, the immune complexes precipitated and recovered by polyethylene glycol is reacted with the complement in serum of a healthy human, and the quantity of the immune complexes were determined by measuring the quantity of the remaining complement based on the hemolysis amount of erythrocytes bonded with the antibody. The operation procedures and conditions of this method are as follows.

(1) 0.3 ml of the sample was poured into a separating tube into which 50 μl of 0.2 M EDTA was added and the mixture was stirred. Then, 50 μl of boric buffer solution (PBS) was further added and the mixture was stirred. Then, 0.1 ml of 12.5% PEG (polyethylene glycol) (molecular weight=7,500) was added and the mixture was stirred. Then, the mixture was allowed to stand at 4° C. for 90 minutes.

(2) The mixture was subjected to centrifugal separation at 4° C. under a load of 1,700 g for 10 minutes. The obtained precipitate was washed with 1.0 ml of 2.5% PEG. Then, centrifugal separation was carried out under a load of 1,700 g for 15 minutes, and the supernatant was discarded.

(3) 30 μl of GVB++ (gelatin-Veronal buffer containing a divalent cation) maintained at 37° C. was added to the precipitate to dissolve the precipitate, and 10 μl of pooled serum of a healthy human was added as the complement source. The immune complexes were reacted with the complement at 37° C. for 30 minutes.

(4) 1.0 ml of EA (antibody sensitized erythrocytes) ($1.5 \times 10^8$ erythrocytes per ml) was added and the mixture was shaken at 37° C. for 60 minutes to promote the hemolysis reaction by the remaining complement.

(5) After completion of the reaction, 6.5 ml of a physiological saline solution maintained at 4° C. was added and the mixture was subjected to centrifugal separation, and the absorbency ($OD_{4/4}$) of the supernatant was measured.

(6) The hemolysis inhibition ratio (unit: PEG-cc %) to the control (serum of a healthy man) was calculated according to the following formula:

$$\text{Inhibition ratio (\%)} = \frac{\text{Absorbancy of control} - \text{Absorbancy of sample}}{\text{Absorbancy of control}} \times 100$$

$$\text{Removal ratio (\%)} = \frac{\text{Inhibition ratio of untreated plasma} - \text{Inhibition ratio of treated plasma}}{\text{Inhibition ratio of untreated plasma}} \times 100$$

Sensitized erythrocytes for the measurement of the complement value (KW), supplied by Nippon Toketsu Kanso Kenkyusho, were used as the EA.

Unactivated Sepharose was used as the control and the above procedures were repeated. The removal ratio was determined, based on the supposition that the removal ratio in the case of the control was 0%. The obtained results are shown in Table 1.

From the results shown in Table 1, it is seen that 4-aminodiphenylamine as the hydrophobic compound can specifically adsorb and remove the rheumatoid factor and immune complexes at a high efficiency.

TABLE 1

| Albumin Removal Ratio (%) | Globulin Removal Ratio (%) | Rheumatoid Factor Removal Ratio (%) | | Immune Complex Removal Ratio (%) |
| --- | --- | --- | --- | --- |
| | | Latex | RAHA | |
| 2 | 25 | 50 | 50 | 40 |

EXAMPLE 2

The procedures of Example 1 were repeated by using tryptophane, tryptophane methyl ester, tryptamine or l-phenylalanine methyl ester instead of 4-aminodiphenylamine. The obtained results are shown in Table 2.

TABLE 2

| Low-Molecular-Weight Organic Compound | Albumin Removal Ratio (%) | Globulin Removal Ratio (%) | Rheumatoid Factor Removal Ratio (%) | | Immune Complex Removal Ratio (%) |
| --- | --- | --- | --- | --- | --- |
| | | | Latex | RAHA | |
| L-tryptophane | 9 | 51 | 75 | 75 | 65 |
| L-tryptophane methyl ester | 6 | 60 | 98 | 98 | 86 |
| Tryptamine | 7 | 59 | 98 | 98 | 89 |
| L-phenylalanine methyl ester | 9 | 41 | 75 | 75 | 63 |

From the results shown in Table 2, it is seen that aromatic ring-containing compounds can specifically adsorb the rheumatoid factor and immune complexes.

EXAMPLE 3

The procedures of Example 2 were repeated by using plasma of a patient suffering from systemic lupus erythematodes, instead of plasma of a patient suffering from rheumatoid arthritis. The obtained results are shown in Table 3.

TABLE 3

| Low-Molecular-Weight Organic Compound | Albumin Removal Ratio (%) | Globulin Removal Ratio (%) | Immune Complex Removal Ratio (%) | Anti-DNA Antibody Removal Ratio (%) |
|---|---|---|---|---|
| L-tryptophane | 8 | 50 | 62 | 75 |
| L-tryptophane methyl ester | 5 | 59 | 82 | 75 |
| Tryptamine | 6 | 61 | 86 | 75 |
| L-phenylalanine methyl ester | 9 | 40 | 61 | 75 |

From the results shown in Table 3, it is seen that aromatic ring-containing compounds can specifically adsorb the immune complexes and anti-DNA antibody from the plasma of a patient suffering from systemic lupus erythematodes at a high efficiency.

Incidentally, the anti-DNA antibody was measured by the testing method utilizing the phenomenon in which, when formalin-fixed chicken hematocytes sensitized by DNA are reacted with plasma of a patient containing the anti-DNA antigen, agglutination of the chicken hematocytes is caused to occur. Other procedures were the same as those adopted in the latex fixation test method. The measurement of the quantity of the anti-DNA antibody was carried out by using a DNA test kit (supplied by Fuji Zoki Seiyaku K. K.).

EXAMPLE 4

According to the N-carboxylic anhydride method, 1:1 oligopetides of d,l-lysine with d,l-tryptophane or d,l-phenylalanine were synthesized by using n-hexylamine as the initiator. The ε-amino group of lysine was protected in advance by a carbobenzoxy group, and the protecting group was removed according to the customary method after synthesis of the oligopeptide. The degree of polymerization (number average polymerization degree) of the formed oligopeptide was determined by measuring the terminal amino group by fluorescent analysis, in the same manner as in Example 1. Each oligopeptide was bonded with activated CH-Sepharose 4B, according to the customary method, blocked with a glycine buffer solution, washed and subjected to the same experiments as those conducted in Example 1. CH-Sepharose 4B blocked with ethanolamine was used as the control. The obtained results are shown in Table 4.

TABLE 4

| | Degree of Retention | | Removal Ratio (%) | | | |
|---|---|---|---|---|---|---|
| | Polymerization | Quantity (mg/m) | Albumin | Globulin | Rheumatoid Factor (latex method) | Immune Complexes |
| Tryptophanelysine | 6.2 | 4.3 | 3 | 65 | 98 | 89 |
| Phenylalanine-lysine | 6.4 | 4.1 | 2 | 60 | 98 | 90 |

From the results shown in Table 4, it is seen that polymers containing a hydrophobic amino acid (hydrophobic compound) can specifically adsorb and remove the rheumatoid factor and immune complexes.

EXAMPLE 5

A homogeneous liquid mixture of 100 g of vinyl acetate, 24.1 g of triallyl isocyanurate (X=0.20), 124 g of ethyl acetate, 124 g of heptane, 3.1 g of polyvinyl acetate (polymerization degree=500) and 3.1 g of 2,2'-azobisisobutyronitrile and a solution, containing 1% by weight of polyvinyl alcohol, 0.05% by weight of sodium dihydrogenphosphate dihydrate and 1.5% by weight of disodium hydrogenphosphate dodecahydrate in 400 ml of water, were charged in a flask, and the mixture was sufficiently stirred and heated with stirring at 65° C. for 18 hours and at 75° C. for 5 hours to effect suspension polymerization and obtain a granular copolymer. The obtained copolymer was recovered by filtration, washed with water, extracted with acetone and subjected to an ester exchange reaction in a solution comprising 46.5 g of sodium hydroxide and 2 l of methanol at 40° C. for 18 hours. The average particle size of the obtained particles was 150 μm. When the hydroxyl group density (gOH) was determined, according to the above-mentioned method, it was found that the hydroxyl group density was 13 meg/g.

The so-obtained gel was packed in a stainless steel column having an inner diameter of 7.5 mm and a length of 25 cm, and an aqueous solution, containing dextrans and polyethylene glycols differing in the molecular weight, or a phosphate buffer solution, containing albumin, immunoglobulin G, immunoglobulin M and β-lypoprotein, was passed through the column. The substances were sequentially dissolved out in the order of their molecular weight. The critical dextran displacement molecular weight was about $3 \times 10^5$ and the critical protein displacement molecular weight was about $18 \times 10^6$. When a solution of human γ-globulin and human albumin in an aqueous solution containing 0.3 M sodium chloride and 0.1 M sodium phosphate as the solvent was passed through the column, both the substances were recovered substantially completely. Thus, it was confirmed that non-specific adsorption was considerably controlled. In each test, the flow rate was adjusted to 1 ml/min.

Then, 50 cc of a gel, which had been ester-exchanged and washed sufficiently with water, was suspended in 200 ml of water, and 3 g of cyanogen bromide was added and the mixture was stirred. Reaction was carried out for 8 minutes while maintaining the pH value at 10 to 11 by using a 2 N aqueous solution of sodium hydroxide. After completion of the reaction, the reaction mixture was promptly filtered by using a glass filter and washed with 2 l of water to obtain an activated gel.

According to the customary method, a l-tryptophane methyl ester was fixed to the so-obtained activated gel and the excessive active groups were blocked with ethanolamine. The retention quantity was determined by reacting and bonding the remaining primary amino groups of the l-tryptophane methyl ester with 4-phenyl-spiro[furan-2(3H)-1'-phthalan]-3,3'-dione ("Furlam ®" supplied by Roche Co.), conducting the measurement with fluorescent rays of 475 to 490 nm (exciting waves of 390 nm) and subtracting the physical adsorption quantity, obtained separately by using unactivated Sepharose 4B, from the measured quantity.

After blocking with ethanolamine, the adsorbing member was washed repeatedly with a 0.1 M acetic acid buffer solution having a pH value of 4 and a 0.1 M boric acid buffer solution having a pH value of 8.5, and the adsorbing member was then washed with a physiological saline solution, hydro-extracted and used for the experiments.

In the adsorption experiment, plasma of a patient suffering from rheumatoid arthritis was mixed with the immune adsorbent at a volume ratio of 3:1 and the mixture was incubated at 37° C. for 3 hours. The quantities of globulin and albumin, after the adsorption, were measured by using an A/G test kit (A/G B Test Kit Wako supplied by Wako Junyaku Kogyo, K. K.). Other experiments were carried out according to the test methods described in Example 1.

Unactivated gel was used as the control and the above procedures were repeated. The removal ratio was determined based on the supposition that the removal ratio, in the case of the control, was 0%. The obtained results are shown in Table 5.

TABLE 5

| Albumin Removal Ratio (%) | Globulin Removal Ratio (%) | Rheumatoid Factor Removal Ratio (%) | | Immune Complex Removal Ratio (%) |
|---|---|---|---|---|
| | | Latex test | RAHA test | |
| 4 | 46 | 87.5 | 93.8 | 66.7 |

From the results shown in Table 5, it is seen that an l-tryptophane methyl ester bonded to the carrier of the present invention can adsorb globulin compounds in plasma, especially the rheumatoid factor and immune complexes, at a high efficiency. The complement value was measured before and after the adsorption. It was found that reduction of the complement value was very slight in each case.

EXAMPLE 6

Experiments were conducted on various hydrophobic compounds in the same manner as described in Example 5. The obtained results are shown in Table 6.

TABLE 6

| Hydrophobic Compound | Retention Amount (mg/m) | Adsorption Ratio (%) | | Rheumatoid Factor Removal Ratio (%) | | Immune Complex Ratio (%) |
|---|---|---|---|---|---|---|
| | | Globulin | Albumin | Latex | RAHA | |
| cyclohexylamine | 2.4 | 10 | 1 | 50 | 50 | 62.1 |
| isoleucine methyl ester | 3.1 | 18 | 3 | 50 | 50 | 63.5 |
| p-aminoaceto-anilide | 2.2 | 21 | 1 | 75.0 | 75.0 | 64.7 |
| a-aminoanthra-cene | 1.7 | 17 | 1 | 75.0 | 75.0 | 64.1 |
| l-phenylalanine methyl ester | 2.9 | 36 | 4 | 75.0 | 81.3 | 66.2 |
| tryptamine | 3.2 | 40 | 5 | 87.5 | 93.8 | 74.6 |

EXAMPLE 7

The blood purifying apparatus shown in FIG. 2 was assembled by using the plasma separating device, having the structure shown in FIG. 5, and the plasma purifying device, having the structure shown in FIG. 1. As the plasma separating membrane, 100 cellulose acetate hollow fibers (having an outer diameter of 450 μm, an inner diameter of 300 μm, an effective length of 115 mm and an average pore size of 0.3 μm) were used, and the plasma purifying device was constructed by packing 10 ml of an immune adsorbent, prepared by bonding an l-tryptophane ethyl ester to CNBr-activated Sepharose 4B (supplied by Pharmacia Co., Sweden; average particle size=260 μm), according to the customary method and blocking the excessive active groups with ethanolamine. By using this blood purifying apparatus, 50 ml of blood of a patient suffering from rheumatoid arthritis was treated for 2 hours at a blood flow rate of 3 ml/min under a pressure difference of 50 mmHg before and after the membrane. Plasma free of erythrocytes and platelets was obtained at a rate of 0.6 ml/min, and purified blood was obtained substantially constantly without hemolysis. Before the treatment, the blood had an albumin concentration of 3.4 g/dl, a γ-globulin concentration of 1.8 g/dl and a rheumatoid factor negation dilution ratio of 1,240. After the treatment, the albumin concentration, γ-globulin concentration and rheumatoid factor negation dilution ratio were reduced to 3.2 g/dl, 1.1 g/dl and 360, respectively. The immune complexes content was reduced by 69% by the treatment.

EXAMPLE 8

The blood treatment was carried out in the same manner as in Example 7, except that a tryptophane methyl ester was used as the hydrophobic organic compound, and blood of a patient suffering from systemic lupus erythematodes was treated. Before the treatment, the blood had an albumin concentration of 3.3 g/dl, a γ-globulin concentration of 1.9 g/dl and an antinuclear antibody negation dilution ratio of 640. After the treatment, the albumin concentration, γ-globulin concentration and antinuclear antibody negation dilution ratio were reduced to 3.1 g/dl, 1.2 g/dl and 320, respectively. The immune complexes content was reduced by 67% by the treatment.

As will be apparent from the foregoing description, when the immune adsorbent, adsorption device and blood purifying apparatus of the present invention are used, injurious autoantibody and/or immune complexes can be removed from blood at a very high efficiency without damaging the hematocyte components and the present invention is very effective for the remedy of collagen diseases, such rheumatoid arthritis.

We claim:

1. An adsorbing material for an autoantibody and/or immune complexes, which comprises (a) an insoluble carrier and (b) an organic low-molecular-weight compound containing a hydrophobic compound having a solubility of not more than 100 millimoles in one dl of a physiological saline solution at 25° C., said organic low-molecular-weight compound being fixed to the insoluble carrier by covalent bonding and having a molecular weight not higher than about 10,000.

2. An adsorbing material as set forth in claim 1, wherein the hydrophobic compound is a compound containing at least one aromatic ring.

3. An adsorbing material as set forth in claim 2, wherein the aromatic ring is an indole ring.

4. An adsorbing material as set forth in claim 1, wherein the organic low-molecular-weight compound containing the hydrophobic compound is a derivative of a hydrophobic amino acid prepared by chemically modifying the hydrophobic amino acid.

5. An adsorbing material as set forth in claim 4, wherein the hydrophobic amino acid is tryptophane.

6. An adsorbing material as set forth in claim 1, wherein the insoluble carrier is of a particulate form having an average particle size of from 25 to 2,500 μm.

7. An adsorbing material as set forth in claim 1, wherein the insoluble carrier is of a fibrous form having a diameter of from 0.02 to 10 denier.

8. An adsorbing material as set forth in claim 1, wherein the insoluble carrier is a crosslinked copolymer containing hydroxyl groups.

9. An adsorbing material as set forth in claim 8, wherein the hydroxyl group-containing crosslinked copolymer is a crosslinked copolymer comprising vinyl alcohol units as the main constituent units.

10. An adsorbing material as set forth in claim 9, wherein the crosslinked copolymer, comprising vinyl alcohol units as the main constituent, is a crosslinked polyvinyl alcohol obtained by hydrolyzing a copolymer of a vinyl ester of a carboxylic acid with a vinyl compound containing an isocyanurate ring.

11. An adsorbing material as set forth in claim 1, wherein the organic low-molecular-weight compound has a molecular weight not higher than about 1,000.

12. An adsorbing device for an autoantibody and/or immune complexes, which comprises a vessel having fluid inlet and outlet openings and an adsorbing material contained in said vessel, said adsorbing material comprising (a) an insoluble carrier and (b) an organic low-molecular-weight compound containing a hydrophobic compound having a solubility of not more than 100 millimoles in one dl of a physiological saline solution at 25° C., said organic low-molecular-weight compound being fixed to the insoluble carrier by covalent bonding and having a molecular weight not higher than about 10,000.

13. A blood purifying apparatus for adsorbing and removing an autoantibody and/or immune complexes from blood plasma, which comprises a blood introduction zone, a purified blood discharge zone, a blood circulation passage including a plasma separating device and a blood-plasma mixing device, and a plasma recycle passage connected to said blood circulation passage to introduce plasma, separated in the plasma separating device, into said mixing device, through a plasma purifying device, said circulation passage and recycle passage being disposed between said blood introduction zone and said purified blood discharge zone, wherein said plasma purifying device comprises a vessel having fluid inlet and outlet openings and an adsorbing material contained in said vessel, said adsorbing material comprising (a) an insoluble carrier and (b) an organic low-molecular-weight compound containing a hydrophobic compound having a solubility of not more than 100 millimoles in one dl of a physiological saline solution at 25° C., said low-molecular-weight compound being fixed to the insoluble carrier and having a molecular weight not higher than about 10,000.

14. A blood purifying apparatus as set forth in claim 13, wherein the plasma separating device comprises a blood inlet, an outlet for concentrated blood, a porous membrane allowing passage of plasma components, but not allowing passage of hematocyte components, a space for temporarily storing separated plasma and a plasma outlet, separated from said blood inlet and outlet by said porous membrane.

15. A blood purifying apparatus as set forth in claim 14, wherein the porous membrane of the plasma separating device is a porous membrane having micropores having an average pore size of 0.05 to 2.0 μm, which are uniformly distributed on the surface of the membrane.

16. A blood purifying apparatus as set forth in claim 13, wherein the plasma separating device is a centrifugal separating device in which blood is continuously introduced from one side and hematocyte-concentrated blood and plasma are continuously discharged, independently, from the other side.

* * * * *